US00PP33326P2

(12) United States Plant Patent
Bedard

(10) Patent No.: US PP33,326 P2
(45) Date of Patent: Aug. 10, 2021

(54) HYBRID TEA ROSE PLANT NAMED 'WEKMOSTADABRE'

(50) Latin Name: *Rosa hybrida*
Varietal Denomination: WEKmostadabre

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/247,433

(22) Filed: Dec. 10, 2020

(51) Int. Cl.
*A01H 5/02* (2018.01)
*A01H 6/74* (2018.01)

(52) U.S. Cl.
USPC ..... Plt./132

(58) Field of Classification Search
USPC ..... Plt./101, 130, 132
See application file for complete search history.

(56) References Cited

U.S. PATENT DOCUMENTS

PP15,334 P2 11/2004 Fryer
PP17,097 P2 9/2006 Zary

OTHER PUBLICATIONS

Weeks Roses, "All Dressed Up", Wholesale Rose Catalog, 86 pages, 2019.

*Primary Examiner* — Susan McCormick Ewoldt
(74) *Attorney, Agent, or Firm* — McKee, Voorhees & Sease, PLC

(57) ABSTRACT

A new variety of Hybrid Tea rose plant suitable for garden decoration, having flowers of hand-painted pink with cream reverse coloration.

1 Drawing Sheet

Classification: The present invention relates to a new *Rosa hybrida* plant.

Variety denomination: The new plant has the varietal denomination 'WEKmostadabre'.

BACKGROUND OF THE INVENTION

This invention relates to a new and distinct variety of Hybrid Tea Rose. It has a non-disseminated seedling of my creation as its seed parent with the following genetic origin Moonstone x Stainless Steel and as its pollen parent the variety known as 'FRYcentury' (U.S. Plant Pat. No. 15,334).

SUMMARY OF THE INVENTION

Among the features which distinguish the new variety from other presently available and commercial rose cultivars known to the inventor are the following combinations of characteristics: its elegant high centered flower, its unique hand-painted pink with cream reverse flower coloration and its excellent color stability throughout the life of the flower. The plant has a bushy upright moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKmostadabre' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKmostadabre' bears double flowers (about 23 to 31 petals) of hand-painted pink with cream reverse coloration, the non-disseminated seedling bears double flowers of magenta pink with cream reverse coloration with significantly lesser petalage (about 18 to 22 petals). The new variety bears flowers with a slight tea to fruity fragrance, whereas the seed parent bears flowers with a strong tea fragrance.

The new variety may be distinguished from its pollen parent, 'FRYcentury' by the following combination of characteristics: whereas 'WEKmostadabre' bears medium to large sized flowers (about 8.6 to about 12.1 cm. in diameter) of hand-painted pink with cream reverse coloration, 'FRYcentury' bears smaller flowers (about 8.0 to about 10.0 cm. in diameter) of pale peach and pink coloration. The new variety has a bushy upright moderately spreading medium to moderately tall growing habit (about 95 to about 172 cm. in height), whereas the pollen parent has a bushy, upright, slightly spreading, medium height shorter growing habit (about 125 to about 150 cm. in height).

COMPARISON WITH THE CLOSEST COMMERCIALLY AVAILABLE CULTIVAR

The new variety may be distinguished from its closest commercially available cultivar, 'JACwypin' (U.S. Plant Pat. No. 17,097) by the following combination of characteristics: whereas 'WEKmostadabre' bears medium to large sized flowers (about 8.6 to about 12.1 cm. in diameter) of hand-painted pink with cream reverse coloration, 'JACwypin' bears larger flowers (about 11.0 to about 12.0 cm. in diameter) of pink with white reverse coloration. The new variety bears flowers with a slight tea to fruity fragrance, whereas the closest commercially available cultivar bears flowers with a strong fruity fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Rancho Cucamonga, Calif. in the month of December. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Rancho Cucamonga, Calif. in the month of December. Phenotypic expression may vary with environmental, cultural and climatic conditions, as well as differences in conditions of light and soil.

FLOWER

The new variety usually bears its flowers singly. Flowers are borne on strong medium to long stems (about 23 to about 75 cm.). Outdoors, the plant blooms abundantly and nearly continuously during the growing season. The flowers have a slight tea to fruity fragrance.

BUD

The peduncle is about 3.2 to about 5.9 cm. in length, of average caliper (about 0.3 to about 0.4 cm. in diameter), and usually erect to moderately stiff. It is somewhat rough, with few stipitate glands and few hairs. Peduncle color is between 146B and 137C sometimes moderately suffused, especially on the side exposed to the sun, with between 187A and 187B.

Before the calyx breaks, the bud is about 1.2 to about 2.2 cm. in diameter at the widest point, about 1.5 to about 2.9 cm. in length, and pointed to somewhat ovoid in shape. The surface of the bud bears between 7 to 9 foliaceous appendages, usually with slender entire foliaceous parts extending beyond the tip of the bud about ½ or more of its length. Bud color is between 137C and 137D sometimes moderately suffused, especially on the side exposed to the sun, with between 187B and 187A.

The sepals are 5 per flower, about 2.0 to about 4.9 cm. in length and about 0.6 to about 1.1 cm. in width at the widest point. The outer surface color of the sepal is between 137C and 137D sometimes moderately suffused, especially on the side exposed to the sun, with between 187B and 187A. The outer surface of the sepal is smooth and bears between 0 to 4 foliaceous appendages with few stipitate glands and hairs. The inner surface color of the sepal is near 146D broadly bordered by near 137C. After the sepals open, the inner surface color is often moderately suffused, especially on the area exposed to the sun, with between 187B and 187A. The inner surface of the sepal is covered with fine wooly tomentum; sepal margins are entire and lined with some stipitate glands and hairs. The sepals are moderately permanent, and spear-shaped in shape with acute apices.

The receptacle of the flower is of short length (about 0.3 to about 0.4 cm.) and moderately thin in caliper (about 0.5 to about 0.9 cm. in diameter). The receptacle is cup-shaped in form. Its surface is smooth with some hairs and few stipitate glands and with somewhat thin fleshy walls. The receptacle color is between 146C and 144A sometimes moderately suffused, especially on the side exposed to the sun, with between 187B and 187A.

As the petals open (after the calyx breaks), the bud is about 1.7 to about 2.7 cm. in diameter at the widest point, about 2.4 to about 3.3 cm. in length, and pointed to moderately ovoid in form. The color of the under surfaces of the newly opened petals is between 11B and 4D often heavily blushed on the outermost petals with between 187A and 187B. There is no visible change in coloration at the point where the petal attaches. The color of the upper surfaces of the newly opened petals is between 1C and 154C often very lightly suffused with near 66C on the upper two thirds of the petals. There is no visible change in coloration at the point where the petal attaches.

BLOOM

When fully open, the bloom ranges from about 8.6 to about 12.1 cm. in diameter. Petalage is double with about 23 to 31 petals and about 3 to 15 petaloids irregularly arranged. When partially open, the bloom form is high centered to somewhat cupped, and the petals are somewhat tightly spiraled to cupped with petal edges moderately reflexed outward. When fully open, the bloom form is more cupped, and the petals are loosely cupped to moderately undulated with petal edges moderately reflexed outward.

PETALS

The substance of the petals is heavy and of thick thickness, with upper surfaces slightly shiny and under surfaces slightly shiny to almost matte. The petals are about 2.3 to about 6.4 cm. in length and about 1.4 to about 5.7 cm. in width at the widest point. Petal margins are entire.

The outer petals are moderately obovate to somewhat rounded in shape with rounded apices.

The inner petals are broadly obovate in shape with rounded apices.

Petaloids are about 0.5 to about 3.1 cm. in length and about 0.4 to about 2.7 cm. in width at the widest point. Petaloids are irregularly shaped moderately oblanceolate to somewhat obovate to subulate with rounded apices.

NEWLY OPENED FLOWER

The under surface color of the outer, intermediate and inner petals is between 4D and 155B sometimes moderately suffused on the outer petals with between 60D and 63A. There is no visible change in coloration at the point where the petal attaches. The upper surface color of the outer, intermediate and inner petals is between 4D and 8D usually heavily suffused with between 66D and 66B on the upper two thirds of the petals. There is no visible change in coloration at the point where the petal attaches.

The under and upper surface colors of the petaloids are similar in coloration to the upper and under surfaces of the intermediate and inner petals.

The general tonality of the newly opened flower is between 66D and 66B.

THREE-DAY-OLD FLOWER

The under surface color of the outer petals is between 4D and 155B sometimes moderately suffused with between 61B and 58A. There is no visible change in coloration at the point where the petal attaches. The upper surface color of the outer petals is between 4D and 8D usually lightly suffused with between 67D and 61C on the upper two thirds of the petals. There is no visible change in coloration at the point where the petal attaches.

The under surface color of the intermediate petals is between 4D and 155B. The upper surface color of the intermediate petals is between 4D and 8D usually moderately suffused with between 67D and 61C on the upper two thirds of the petals.

The under surface color of the inner petals is between 4D and 155B. The upper surface color of the inner petals is between 4D and 8D usually heavily suffused with between 61C and 57C on the upper two thirds of the petals.

The under and upper surface colors of the petaloids are similar in coloration to the upper and under surfaces of the inner petals.

The general tonality of the three-day-old flower is between 67D and 61C.

On the spent bloom, the petals usually drop off cleanly.

In December in Rancho Cucamonga, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 105) and are arranged regularly about the pistils; a few are mixed with petaloids. The filaments are of somewhat short to medium length (about 0.4 to about 0.9 cm.) most with anthers. Filaments are between 4D and 2D in color. The anthers are somewhat small for the class and all open approximately at the same time. Anther color when immature is between 10C and 8C. Anther color at maturity is near 164C on the external part and near 200A on the internal part. Pollen is moderate and between 21B and 22B in color.

FEMALE REPRODUCTIVE ORGANS

Pistils vary in number (average about 95). The styles are moderately even, average in length (about 0.6 to about 0.9 cm.), average to somewhat thin in caliper, and loosely bunched. Stigma color is between 13C and 14C. Style color is between 1D and 154D sometimes lightly suffused with between 60A and 60B. Ovaries are usually all enclosed in the calyx. The ovaries are of medium size and between 158B and 158C in color.

Hips have not been observed on this variety when grown in Rancho Cucamonga, Calif.

FOLIAGE

The compound leaves are usually comprised of three to seven leaflets and are borne abundantly. The five-leaflet leaves are about 8.7 to about 12.9 cm. in length and about 7.3 to about 10.7 cm. in width at the widest point, moderately leathery to somewhat crisp in texture on both sides, and glossy in finish on the upper side and semi-glossy to somewhat matte in finish on the under side. The leaves have a pinnate venation pattern. The terminal leaflets are about 4.3 to about 6.8 cm. in length and about 2.5 to about 4.7 cm. in width at the widest point, shaped broadly ovate with acute apices and rounded bases. Their margins are usually simply serrate.

The upper surface color of the mature leaf is between 139A and 137A. The under surface color of the mature leaf is between 147B and 148C. The under and upper colors of the leaf veins on the mature leaf are similar in coloration to the upper and under surfaces colors of the mature leaf. The upper surface color of the young leaf is between 137B and 137C, often heavily suffused with between 187A and 187B. The under surface color of the young leaf is between 146D and 146C, often heavily suffused with between 187A and 187B. The under and upper colors of the leaf veins on the young leaf are similar in coloration to the upper and under surfaces colors of the young leaf.

The rachis is about 4.1 to about 6.3 cm. in length, about 0.1 to about 0.2 cm in width at the widest point, and rough. The upper side is deeply grooved with very few hairs and stipitate glands on the edges of the grooves. The under side of the rachis is rough with few stipitate glands and small prickles. The rachis color is near 146D on the under side and near 137C on the upper side, often heavily suffused on the young leaves with between 187A and 187B.

The stipules are about 0.7 to about 1.1 cm. in length and of somewhat narrow to medium width (about 0.4 to about 0.6 cm.) with somewhat short to medium length straight points that usually turn out at an angle of more than 45 degrees. The under and upper surface color of the stipule is between 137B and 137C. The upper and under surfaces of the stipules are smooth in texture.

The petiole is somewhat light to average in caliper and rough. The upper side is deeply grooved with very few hairs and stipitate glands on the edges of the grooves. The under side of the petiole is rough with few stipitate glands and small prickles. The petiole is about 0.7 to about 1.7 cm. in length and about 0.1 to about 0.2 cm in width at the widest point. The petiole color is near 146D on the under side and near 137C on the upper side, often heavily suffused on the young leaves with between 187A and 187B.

The plant displays an average degree of resistance to powdery mildew (*Sphaerotheca pannosa*), downy mildew (*Peronospora sparsa*) and rust (*Phragmidium* sp.) as compared to other commercial varieties grown under comparable conditions in Rancho Cucamonga, Calif. The plant's winter hardiness and drought/heat tolerance are yet to be determined.

GROWTH

The plant has a bushy upright moderately spreading medium to moderately tall growing habit (about 95 to about 172 cm. in height and about 122 to about 155 cm. spread at the widest point), with full branching. It displays vigorous growth and the canes are of medium to somewhat heavy caliper for the class (about 1.3 to about 2.4 cm. in diameter at the widest point).

The color of the major stems is between 138A and 147B. The major stems are rough in texture and they bear many large prickles that are about 0.7 to about 1.3 cm. in length. The large prickles are almost straight to angled slightly downward with a moderately long somewhat narrow oval base; prickle color is between 165C and 164B often lightly suffused with between 201B and 201C. The major stem bears few small prickles of similar shape and coloration.

The color of the branches is between 146B and 137C. The branches are rough in texture and they bear many large prickles which are of similar size and shape to the large prickles on the major stems; prickle color is between 166A and 165A. The branches bear few small prickles of similar shape and coloration.

The color of the new shoots is between 146B and 137C often heavily suffused with between 187B and 187A. The new shoots are rough in texture and they bear many large prickles which are of similar size and shape to the large prickles on the major stems; prickle color is between 152C and 152B often moderately suffused with between 187D and 187C. The shoots bear few small prickles of similar shape and coloration.

I claim:

1. A new and distinct Hybrid Tea rose plant of the variety substantially as described and illustrated herein.

* * * * *

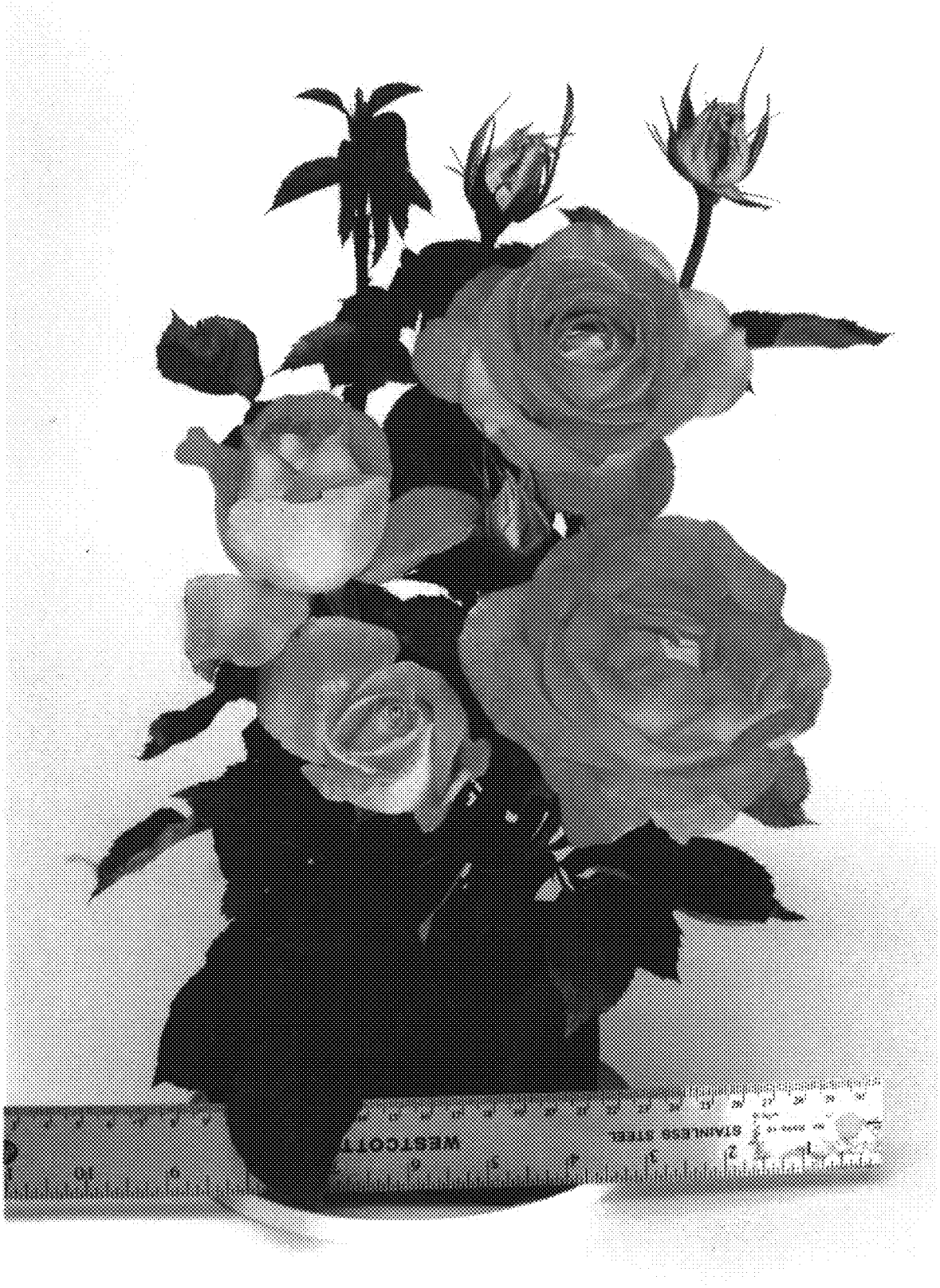
WESTCOTT
STAINLESS STEEL